United States Patent

Dawson

[11] 4,416,892
[45] Nov. 22, 1983

[54] METHOD OF TREATING HYPERSENSITIVITY DISEASE WITH BENZOXAZOLE DERIVATIVES

[75] Inventor: William Dawson, Camberley, England

[73] Assignee: Lilly Industries Limited, London, England

[21] Appl. No.: 368,079

[22] Filed: Apr. 14, 1982

[30] Foreign Application Priority Data

Apr. 23, 1981 [GB] United Kingdom ................. 8112538

[51] Int. Cl.$^3$ ............................................ A61K 31/42
[52] U.S. Cl. ................................................. 424/272
[58] Field of Search ......................................... 424/272

[56] References Cited

PUBLICATIONS

Levine et al.-Arch. Int. Pharmacodyn vol. 230 (1977) pp. 309-318.

*Primary Examiner*—Sam Rosen
*Attorney, Agent, or Firm*—James L. Rowe; Arthur R. Whale

[57] ABSTRACT

The invention relates to a method for the prophylactic or therapeutic treatment of an immediate hypersensitivity disease, which comprises administering to a mammal, including a human, a compound of the following formula

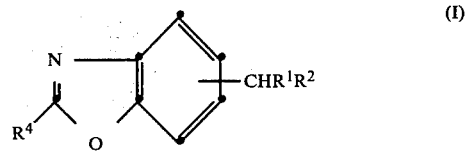

(I)

in which the group —$CHR^1R^2$ is in the 5- or 6- position of the benzoxazole nucleus, $R^1$ is hydrogen or $C_{1-4}$ alkyl, $R^2$ is selected from the group —COOH or a salt or ester thereof, the group —$CONH_2$ and the group —$CH_2OH$, and in which $R^4$ is a phenyl group optionally substituted by one or two groups selected from halogen, $C_{1-4}$ alkoxy, $C_{1-4}$ alkyl and $C_{1-4}$ haloalkyl, or optionally substituted in two adjacent positions by methylenedioxy.

3 Claims, No Drawings

METHOD OF TREATING HYPERSENSITIVITY DISEASE WITH BENZOXAZOLE DERIVATIVES

This invention relates to the use of pharmaceutical compounds in the treatment of disease.

BACKGROUND OF THE INVENTION

British Pat. No. 1435721 discloses a group of benzoxazole compounds of the formula

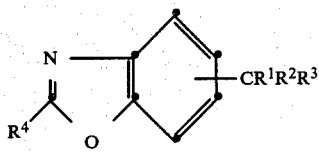

where the group —$CR^1R^2R^3$ is in the 5- or 6-position, and the substituents $R^1$, $R^2$, $R^3$ and $R^4$ take various values, these compounds being described as principally of use in the treatment of anti-inflammatory diseases. We have now discovered that certain of these compounds have useful properties in the treatment of immediate hypersensitivity diseases.

SUMMARY OF THE INVENTION

The invention provides a method for the prophylactic or therapeutic treatment of an immediate hypersensitivity disease, which comprises administering to a mammal, including a human, a compound of the following formula:

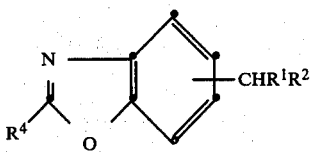

(I)

in which the group —$CHR^1R^2$ is in the 5- or 6- position of the benzoxazole nucleus, $R^1$ is hydrogen or $C_{1-4}$ alkyl, $R^2$ is selected from the group —COOH or a salt or ester thereof, the group —$CONH_2$ and the group —$CH_2OH$, and in which $R^4$ is a phenyl group optionally substituted by one or two groups selected from halogen, $C_{1-4}$ alkoxy, $C_{1-4}$ alkyl and $C_{1-4}$ haloalkyl, or optionally substituted in two adjacent positions by methylenedioxy.

The immediate hypersensitivity disease can be such as for example asthma, status asthmaticus, rhinitis, atopic eczema and urticaria. More particularly the invention includes a method of treating a mammal, including a human, suffering from or susceptible to asthma, which comprises administering to the mammal an amount which is effective for such treatment of a compound of formula (I) above.

DESCRIPTION OF PREFERRED EMBODIMENTS

Reference in the above formula (I) to an ester or salt of the group —COOH means any pharmaceutically acceptable ester or salt. Preferred esters are those in which $R^2$ is —$COOR^5$ and $R^5$ is $C_{1-4}$ alkyl, amino —$C_{1-4}$ alkyl, $C_{1-4}$ alkylamino —$C_{1-4}$ alkyl or di-$C_{1-4}$ alkylamino —$C_{1-4}$ alkyl, and in which $C_{1-4}$ alkyl is, for example, methyl, ethyl, propyl, isopropyl, butyl, t-butyl, and especially methyl or ethyl. Preferred salts are the alkali or alkaline earth metal, aluminium or ammonium salts, and are especially potassium, sodium or ammonium salts. When the $R^4$ group is phenyl substituted with $C_{1-4}$ alkyl the substituent can be any one of the values mentioned above and is preferably methyl. The preferred value of $C_{1-4}$ alkoxy is similarly methoxy, and of $C_{1-4}$ haloalkyl, trifluoromethyl, and halogen is preferably chlorine or fluorine. There can be one or two substituents on the phenyl ring and these can take different values. Such compounds have an optical centre at the carbon atom attached to the benzene ring and thus exist in D, L and racemate forms, all of which are intended to be included in the ambit of this invention.

A preferred group of compounds of formula (I) for use in the method of the invention are those of the formula

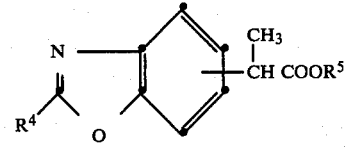

in which $R^4$ is a phenyl group optionally substituted by one or two halogen atoms, and $R^5$ is hydrogen or $C_{1-4}$ alkyl, and when $R^5$ is hydrogen, salts thereof. The free acids and salts are most preferred and those compounds in which the phenyl group is substituted by one or two halogen atoms, one such halogen atom being in the 4-position.

An especially preferred compound is 2-(4-chlorophenyl)-α-methyl-5-benzoxazoleacetic acid, of the formula

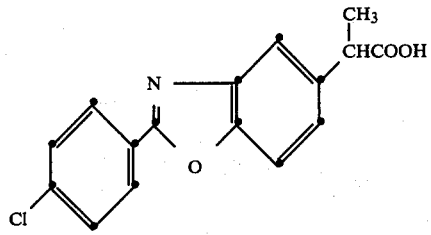

or a salt thereof, and further examples of preferred compounds are
2-(4-fluorophenyl)-α-methyl-5-benzoxazoleacetic acid,
2-(2-chlorophenyl)-α-methyl-6-benzoxazoleacetic acid,
2-(4-chlorophenyl)-α-methyl-6-benzoxazoleacetic acid, and salts of these acids.

The activity of these compounds has been demonstrated in guinea pigs using either the "guinea-pig chopped lung test" described by Mongar and Schild in the Journal of Physiology (London) 131, 207 (1956) or Brocklehurst in the Journal of Physiology (London) 151, 416 (1960), or in the "Herxheimer" test described in the Journal of Physiology (London) 117, 251 (1952). For example, the compounds exhibit a greater than 10 percent inhibition of mediator release in the "guinea-pig chopped lung test". In the "Herxheimer" test, which is based on an allergic bronchospasm induced in guinea pigs closely resembling an asthmatic attack in man, compounds have exhibited activity at dosages ranging from 25 mg/kg to 200 mg/kg. These tests are wellrecognised as indicative of anti-allergy activity in humans and mammals in general.

The compounds may be administered by various routes, although it is a special feature of the compounds that they are effective when administered orally. Thus the compounds may be administered by the oral and rectal routes, topically and parenterally e.g. by injection, being usually employed in the form of a pharmaceutical composition. Such compositions are prepared in a manner well known in the pharmaceutical art and normally comprise at least one active compound in association with a pharmaceutically-acceptable carrier therefor. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus the composition can be in the form of tablets, lozenges, sachets, cachets, elixirs, suspensions, aerosols (as a solid or in a liquid medium), ointments, soft and hard gelatine capsules, suppositories, injection suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propylhydroxybenzoate, talc, magnesium stearate or mineral oil. The compositions of the invention may, as is well known in the art, be formulated so as to provide quick, sustained or delayed release of the active ingredient after administration to the patient.

Preferably the compositions are formulated in a unit dosage form, each dosage containing from 10 to 1500 mg, more usually 50 to 1000 mg, of the active ingredient. The term "unit dosage form" refers to physically discrete units suitable as unitary dosages for human subjects and animals, each unit containing a predetermined quantity of active material calculated to produce the desired therapeutic effect, in association with the required pharmaceutical carrier.

The active compounds are effective over a wide dosage range and for example dosages per day will normally fall within the range of 0.1 to 25 mg/kg and in the treatment of adult humans, more usually in the range of from 1 to 15 mg/kg. However it will be understood that the amount of the compound actually administered will be determined by a physician, in the light of the relevant circumstances including the condition to be treated, the choice of compound to be administered and the chosen route of administration and therefore the above dosage ranges are not intended to limit the scope of the invention in any way.

The following Examples illustrate the invention:

EXAMPLE 1

A formulation containing 300 mg of the compound 2-(4-chlorophenyl)-α-methyl-5-benzoxazoleacetic acid was prepared by mixing the compound with the following ingredients

| | |
|---|---|
| Amberlite IRP 88 (polacrilin potassium) | 20 mg |
| Microcrystalline cellulose | 200 mg |
| Polyvinylpyrrolidone (PVP) | 20 mg |
| Magnesium Stearate | 5 mg | and forming the constituents into a tablet. A tablet containing 600 mg of the active compound was also prepared employing twice the quantity of the above carriers.

EXAMPLE 2

Compounds were tested in the guinea pig chopped lung test referred to above. This is a test regularly used to detect anti-allergy activity for use in the treatment of immediate hypersensitivity diseases, which involves direct measurement of slow reacting substance in anaphylaxis (SRS-A) produced in response to a challenge. SRS-A has been shown to be released by asthmatic human lung.

Male albino guinea pigs (250–350 g) were sensitised with ovalbumin (100 mg s/c+100 mg i p.) and three weeks later killed, their lungs removed and perfused clear of blood with Tyrode's solution. The lungs were chopped into 0.5 mm cubes and divided into 400 mg aliquots. After washing and equilibration at 37° C., the aliquots were challenged with antigen in the presence or absence of the test compound. One control group was not challenged and was used to assess non-anaphylactic SRS-A release. Following incubation with rocking at 37° C. for 15 mins, each supernatant was removed and bio-assayed. Results are expressed as the percentage inhibition of SRS-A release after exposure to $3 \times 10^{-5}$ M solutions of test compound. Each result is the mean of four samples.

| | % Inhibition of SRS-A at $3 \times 10^{-5}$M |
|---|---|
| 2-(4-fluorophenyl)-α-methyl-5-benzoxazoleacetic acid | 36 |
| 2-(3-trifluoromethylphenyl)-α-methyl-5-benzoxazoleacetic acid | 27 |
| 2-(2-chlorophenyl)-α-methyl-6-benzoxazoleacetic acid | 16 |
| 2-(4-chlorophenyl)-α-methyl-6-benzoxazoleacetic acid | 38 |
| 2-(4-chlorophenyl)-α-methyl-5-benzoxazoleacetic acid | 62 |

EXAMPLE 3

The compound 2-(4-chlorophenyl)-α-methyl-5-benzoxazoleacetic acid was examined in the Herxheimer test.

Male guinea pigs were sensitised with ovalbumin and then exposed to ovalbumin aerosol (1% w/v solution) in an observation chamber. The animals were kept in the exposure chamber until symptoms of respiratory distress, terminating in a characteristic convulsive cough. The time of exposure is the "collapse time". Exposure beyond this end-point resulted in convulsions and death from severe bronchospasm. Histamine is known to play a significant part in the observed bronchospasm, and pre-treatment with the anti-histamine mepyramine reveals that a non-histamine component is responsible for the remainder of the response. Accordingly, the response to each compound in the presence of mepyramine (0.5 mg/kg s.c.) given half an hour before challenge was studied. The compound itself was given orally four hours before antigen challenge. A protection ratio of 1.4 or greater is considered significant.

The protection ratio $\frac{(M + D)}{M}$ was defined as:

$$\frac{\text{Mean collapse time after pre-treatment with mepyramine (M) + compound (D)}}{\text{Mean collapse time of control animals with mepyramine (M)}}$$

| Dose mg/kg | $\frac{D + M}{M}$ |
|---|---|
| 25 | 2.1 |
| 25 | 1.4 |
| 25 | 2.9 |
| 50 | 2.7 |

What I claim is:

1. A method for the therapeutic treatment of an immediate hypersensitivity disease, which comprises administering to a mammal, including a human, a compound of the following formula

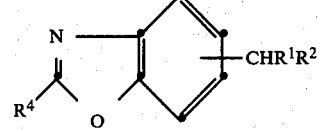

(I)

in which the group —$CHR^1R^2$ is in the 5- or 6- position of the benzoxazole nucleus, $R^1$ is hydrogen or $C_{1-4}$ alkyl, $R^2$ is selected from the group —COOH or a salt or ester thereof, the group —$CONH_2$ and the group —$CH_2OH$, and in which $R^4$ is a phenyl group optionally substituted by one or two groups selected from halogen, $C_{1-4}$ alkoxy, $C_{1-4}$ alkyl and $C_{1-4}$ haloalkyl, or optionally substituted in two adjacent positions by methylenedioxy.

2. A method according to claim 1 which comprises administering a compound of the formula

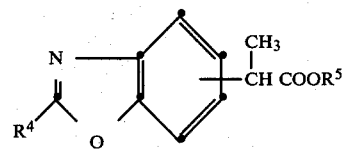

in which $R^4$ is a phenyl group optionally substituted by one or two halogen atoms, and $R^5$ is hydrogen or $C_{1-4}$ alkyl, and when $R^5$ is hydrogen, salts thereof.

3. A method according to claim 1 which comprises administering 2-(4-chlorophenyl)-α-methyl-5-benzoxazoleacetic acid.

* * * * *